United States Patent
Lee

(10) Patent No.: US 7,125,572 B2
(45) Date of Patent: Oct. 24, 2006

(54) TYROSINASE INHIBITOR EXTRACT

(75) Inventor: Ming Chen Lee, Hsintien (TW)

(73) Assignee: Kaoder Industry Company, Ltd. (TW)

( * ) Notice: Subject to any disclaimer, the term of this patent is extended or adjusted under 35 U.S.C. 154(b) by 268 days.

(21) Appl. No.: 10/846,008

(22) Filed: May 14, 2004

(65) Prior Publication Data

US 2005/0255181 A1  Nov. 17, 2005

(51) Int. Cl.
*A61K 36/752* (2006.01)
*A61K 36/00* (2006.01)

(52) U.S. Cl. .................................. 424/736; 424/725

(58) Field of Classification Search ............... 424/736, 424/725
See application file for complete search history.

(56) References Cited

U.S. PATENT DOCUMENTS

| | | |
|---|---|---|
| 5,523,077 A | 6/1996 | Pawelek et al. |
| 5,980,904 A * | 11/1999 | Leverett et al. ............. 424/725 |
| 6,365,137 B1 | 4/2002 | Aust et al. |
| 2002/0141955 A1* | 10/2002 | Zimmerman et al. ......... 424/62 |

FOREIGN PATENT DOCUMENTS

JP      410316533 A  * 12/1998

* cited by examiner

*Primary Examiner*—Patricia Leith
(74) *Attorney, Agent, or Firm*—Ladas & Parry LLP

(57) ABSTRACT

The present invention discloses a tyrosinase inhibitor extract from lemon peels. The tyrosinase inhibitor extract contains a tyrosinase inhibitor content and provides advantageous skin whitening effects.

16 Claims, 4 Drawing Sheets

A

B

A

B

C

TYROSINASE INHIBITOR EXTRACT

BACKGROUND OF THE INVENTION

1. Field of the Invention

The present invention relates to a tyrosinase inhibitor extract from lemon peels.

2. Description of the Prior Art

Melanin plays an important role in protecting human body from the harmful effects of ultraviolet rays. Melanin is also an important factor in medical science and cosmetology. It is known that melanin is formed or synthesized in skin tissues. Excessive amounts of melanin darken the skin, and the nonuniform distribution of melanin causes chloasma and ephelis, both of which are skin disorders. The biosynthesis pathway of melanin involves the catalytic hydroxylation of tyrosine to L-3,4-dihydroxyphenylalanine (L-DOPA) and the conversion of L-DOPA to dopachrome. The more effective way to inhibit the synthesis of melanin is to block the hydroxylation of tyrosine.

Conventionally, tyrosinase inhibitors have been used to decrease the level of melanin in the skin and thereby produce a lightly pigmented skin. A variety of whitening cosmetics have been proposed or investigated and developed in order to remove spots, such as stains, and freckles, appearing on the skin and to provide a whitening effect on the skin. For example, peroxides, ascorbic acid, kojic acid, hydroquinone, glutathione, arbutin and cysteine have been developed to whiten skin. However, the conventional whitening agents have various disadvantages. For example, peroxides are unstable and have little effects on reducing the pigmentation in practical applications. Ascorbic acid is not an effective whitening agent because of its low activity in inhibiting tyrosinase and low stability. U.S. Pat. No. 6,365,137 indicates that kojic acid can be used as an inhibitor of tyrosinase. Kojic acid inhibits the activity of the enzyme by chelating the active site of tyrosinase with a copper ion. However, is it not appropriate to use kojic acid in cosmetics because it is unstable in the process of cosmetics. U.S. Pat. No. 5,523,077 mentions that hydroquinone can be used as a whitening agent. Hydroquinone is a competitive inhibitor, which causes adverse effects in skin such as irritation.

There has been a high demand of medicines or cosmetic which have advantageous skin whitening effects without adverse effects.

SUMMARY OF THE INVENTION

An object of the invention is to provide a tyrosine inhibitor extract, which is obtainable by the process comprising the steps of:
  a) mixing lemon peels with a propylene glycol solution;
  b) breaking the cell walls of the lemon peels whereby the tyrosinase inhibitor content therein is extracted into the propylene glycol solution; and
  c) removing the lemon peels.

Another objective of the invention is to provide a tyrosinase inhibitor extract, which comprises the following characteristics:
  i) having an optimal pH between 7.0 and 9.0;
  ii) having an absorbance at 280 nm;
  iii) being a non-competitive inhibitor;
  iv) having inhibitory effect on tyrosinase over 80% at body temperature; and
  v) being stable and not prone to color change under light and heat.

A further object of the invention is to provide a process for preparing a tyrosinase inhibitor extract, comprising the steps of:
  a) mixing lemon peels with a propylene glycol solution;
  b) breaking the cell walls of the lemon peels whereby the tyrosinase inhibitor content therein is extracted into the propylene glycol solution; and
  c) removing the lemon peels.

DETAILED DESCRIPTION OF THE INVENTION

Figure 1:
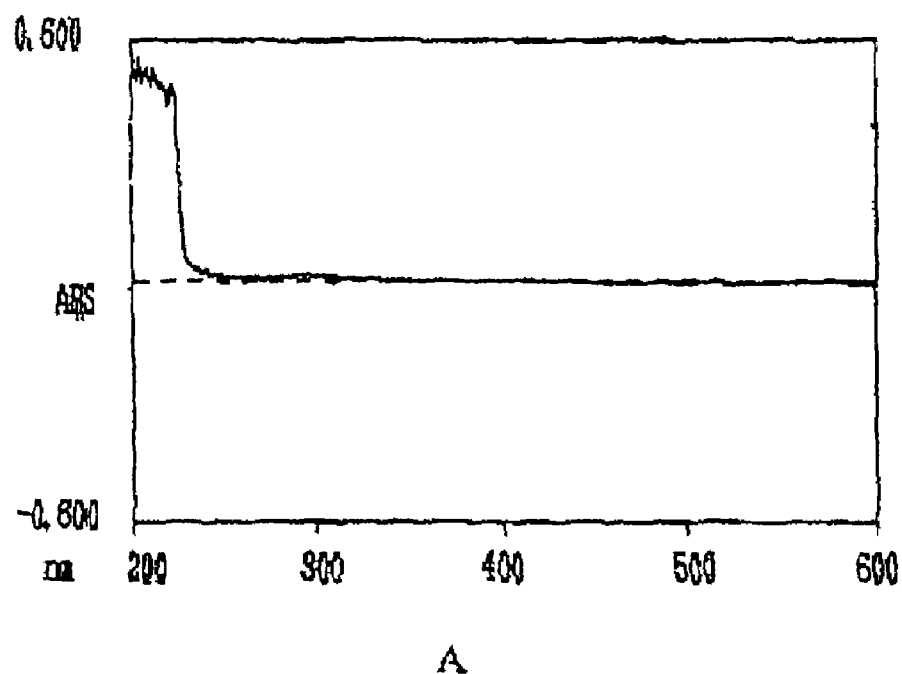
FIG. 1 shows the absorbance of the tyrosinase inhibitor extract of the invention and the control; (A) control (80% propylene glycol), and (B) the tyrosinase inhibitor extract of the invention.
Figure 1:
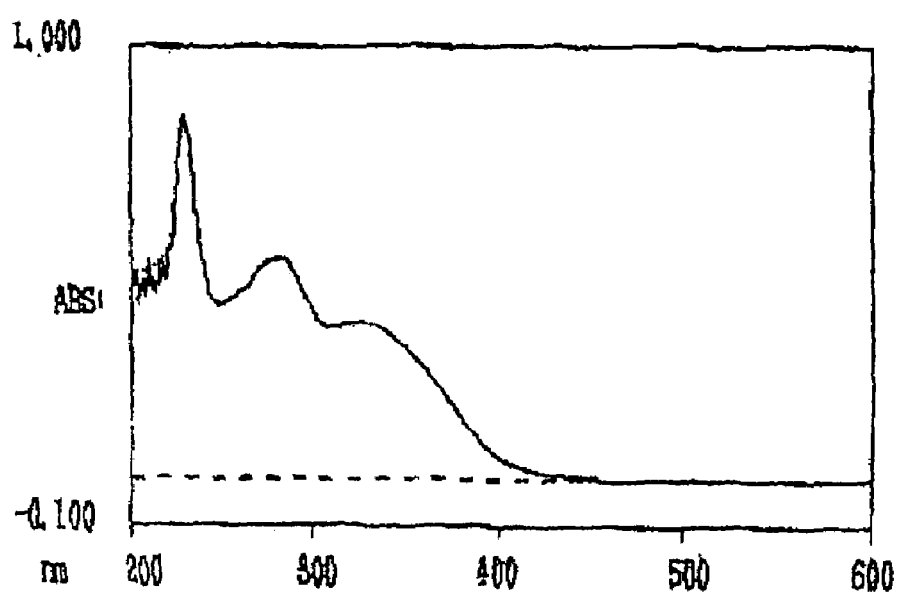

It is surprisingly found that the propylene glycol extract of lemon peels exhibits a tyrosinase inhibitory effect and provides advantageous skin whitening effect.

The present invention provides a tyrosinase inhibitor extract, which is obtainable by the process comprising the steps of:
  a) mixing lemon peels with a propylene glycol solution;
  b) breaking the cell walls of the lemon peels whereby the tyrosinase inhibitor content therein is extracted into the propylene glycol solution; and
  c) removing the lemon peels.

According to the invention, it is desirable to treat lemons while they are as fresh as possible. The lemon peels used as the starting material are optionally cut into pieces of an appropriate size. The lemon peels are mixed with a propylene glycol solution. Skilled artisans can determine the level and concentration of the propylene glycol solution to be used in extracting the tyrosinase inhibitor extract of the invention according to the amount of the lemon peels. Preferably, the concentration of propylene glycol in the solution is higher than 50%. More preferably, the concentration of propylene glycol is higher than 70%. Most preferably, the concentration of propylene glycol is higher than 80%. Preferably, the ratio of the lemon peels to the propylene glycol solution ranges from 0.1 g/ml to 1 g/ml, more preferably 0.2 g/ml to 0.8 g/ml.

According to the invention, the cell walls of lemon peels are broken so that propylene glycol enters into the cells and the tyrosinase inhibitor content therein can be extracted. Any appropriate process can be used to break the cell walls of lemon peels. For example, the cell walls of lemon peels can be broken by sonication, Waring blender, homogenization, French press or Polytron. Preferably, the cell walls are broken by sonication and homogenization. More preferably, the cell walls are broken by sonication. According to the invention, the resulting extract can be further sterilized. High temperature is improper to sterilize the extract solution because the high temperature may destroy the inhibitory activity of the tyrosinase inhibitor content in the extract. The appropriate method includes, but not limited to, microwave, filtration, UV and gamma radiation.

According to the invention, the lemon peels are removed from the resultant solution to obtain a propylene glycol solution containing the tyrosinase inhibitor content. Any appropriate process can be used to remove the lemon peels. For example, the lemon peels can be removed by centrifugation or filtration. Preferably, the lemon peels are removed by centrifugation.

According to the invention, the tyrosinase inhibitor extract of the invention has a main absorbance at 280 nm. This indicates that the tyrosinase inhibitor extract contains a protein or peptide. It is believed that the protein or peptide is the main active component for inhibiting tyrosinase. The other components of the extract may provide additional effects such as anti-aging and anti-oxidation. The optimal pH of the tyrosinase inhibitor extract is between the range of neutral and weak basic values. Preferably, the optimal pH of the tyrosinase inhibitor extract of the invention is between pH 7.0 to pH 9.0. The tyrosinase inhibitor extract of the invention is a non-competitive inhibitor, which can inhibit the synthesis of melanin at a low concentration. The tyrosinase inhibitor extract is stable and not prone to color-change under light and heat. Moreover, the tyrosinase inhibitor extract exhibits an inhibitory effect over 80% at body temperature. Thus, the tyrosinase inhibitor extract has a great potential for use as a whitening ingredient of cosmetics. Furthermore, 90% of inhibition activity of the tyrosinase inhibitor extract can be observed in one hour after application.

The tyrosinase inhibitor extract of the invention may be used in cosmetics to provide whitening effect. The tyrosinase inhibitor extract can be topically applied to affected area as to remove, e.g., freckles and pigment deposits after sunburn.

The tyrosinase inhibitor extract can be prepared to be in various forms, including lotions, emulsions, creams, ointments, sticks, solutions, packs, and gel. The tyrosinase inhibitor extract may be admixed with any ingredients ordinarily used in cosmetics, such as oily substances, humectants, thickeners, preservatives, emulsifiers, medical ingredients, perfumes, emulsification stabilizers and the like. The tyrosinase inhibitor extract may be used in combination with other whitening ingredients, (such as UV absorbers, vitamin C, kojic acid, vitamin E acetate, glycyrrhizin, salicylic acid and arbutin), anti-inflammatory agents, oils, surfactants, moisturizers, animal and vegetable extracts, pH-adjusting agents, colorants, fragrances, preservatives, and chelating agents, with a concentration not interfering with the effect of the extract of the invention.

The following examples further illustrate the present invention, but are not intended to limit the scope of the present invention. The modifications and substitutions known to those skilled in the art are still within the scope and spirit of the present invention.

EXAMPLE

Example 1

Preparation of Tyrosine Inhibitor Extract 100 g of freshly minced lemon peels were mixed with 100–1000 ml of propylene glycol. The resultant solution was sonicated for a few seconds to break the cell walls of the lemon peels, and well mixed. The resultant extract was then sterilized and centrifuged. The supernatant was collected to obtain the tyrosinase inhibitor extract. The yield of 100 g of lemon peels extracted with propylene glycol is 70% to 90% of the volume of propylene glycol used.

Example 2

Main Component of the Tyrosinase Inhibitor Extract

The absorbance at wavelengths 200 nm to 600 nm of the tyrosinase inhibitor extract of the invention and 80% propylene glycol were shown in FIG. 1A and FIG. 1B, respectively. As shown in FIG. 1, the tyrosinase inhibitor extract of the invention contains three main components. The absorbance at wavelength 280 nm indicates that one of the components is a protein or peptide.

Example 3

Determination of Tyrosinase Inhibitory Effect

The activity of tyrosinase was determined at the wavelength of 475 nm and calculated from the decrease of the absorbance. The more whitening effect was shown, the higher percentage of inhibition there was.

35 μl of the tyrosinase inhibitor extract of Example 1 and 35 μl of 80% propylene glycol were used as the test and control samples. The inhibition percent of the tyrosinase activity was calculated by the equation: Inhibition percentage (%) of the tyrosine activity=[1−(Absorbance of experiment sample)/(Absorbance of control sample)]×100%. The DOPA and tyrosinase solution (1000 units/ml in 16.7 mM potassium phosphate butter) used in the following experiments were purchased from Sigma Corp., USA.

Inhibition Percentage of the Tyrosinase Inhibitor Extract on Tyrosinase under Different Reaction Time:

15.1 of tyrosinase solutions was added to each (35 μl) of six samples of tyrosinase inhibitor extract of Example 1. The resultant solutions were maintained at 25. for 0, 1, 2, 3, 4, 5, 6 hours, respectively. 450.1 of L-DOPA substrate was added to each of the solutions. The inhibition percentage of the samples is shown in the table below:

| Time (hours) | % Inhibition |
| --- | --- |
| 0 | 34.0 + −0.8 |
| 1 | 93.5 + −0.8 |
| 2 | 95.4 + −0.9 |
| 3 | 84.6 + −0.6 |
| 4 | 84.2 + −0.8 |
| 5 | 85.7 + −1.6 |
| 6 | 86.2 + −0.4 |

As shown in the table, 90% tyrosinase inhibitory activity can be observed one hour after adding the tyrosinase inhibitor extract of the invention.

Inhibition Percentage of the Tyrosinase Inhibitor Extract on Tyrosinase under Different Temperature The inhibition percentage of the tyrosinase inhibitor extract of Example 1 was determined at 25., 37. and 50., respectively.

15.1 of tyrosinase solutions was added to each (35 μl) of three samples of tyrosinase inhibitor extract of Example 1. The resultant solutions were maintained at 25., 37. and 50. for 1 hour, respectively. 450.1 of L-DOPA substrate was added to each of the solutions. The inhibition percentage of the samples is described in the table below:

| Temperature (□) | % Inhibition Activity |
|---|---|
| 25 | 90.36 |
| 37 | 79.30 |
| 50 | 69.10 |

As shown in the table, the tyrosinase inhibitory effect can reach 80% at body temperature (37.). The extract has a great potential to be used as a whitening ingredient of cosmetics.

Figure 2:
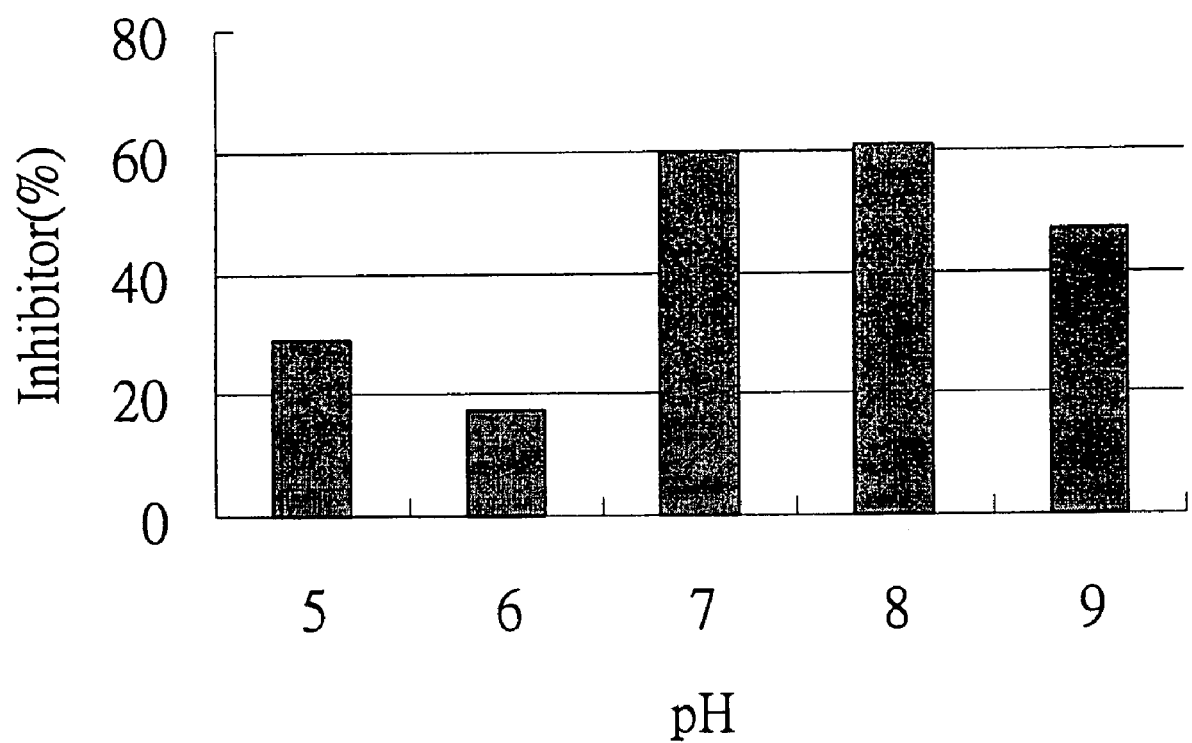
FIG. 2 shows the effect of pH on the inhibitory effect of the tyrosinase inhibitor extract of the invention on tyrosinase.

Inhibition Percentage of the Tyrosinase Inhibitor Extract on Tyrosinase Under Different pH 15.1 of tyrosinase solutions was added to each (35 μl) of five samples of tyrosinase inhibitor extract of Example 1. The resultant solutions were maintained at pH 4, 5, 6, 7 and 8 for 1 hour, respectively. 450.1 of L-DOPA substrate was added to each of the solutions. The inhibition percentage of the samples is shown in the table below and FIG. 2:

| PH | % Inhibitory Activity |
|---|---|
| 4 | — |
| 5 | 29.0 + −3.6 |
| 6 | 17.4 + −2.1 |
| 7 | 60.0 + −4.4 |
| 8 | 60.8 + −3.4 |
| 9 | 47.1 + −1.1 |

As shown in the table, the optimum pH is between 7 and 9. Since the optimal pH ranges from neutral to weak basic pH's, the tyrosinase inhibitor extract of the invention is safe and brings no irritation or allergy to the skin when applying to skin.

Example 4

Figure 3:
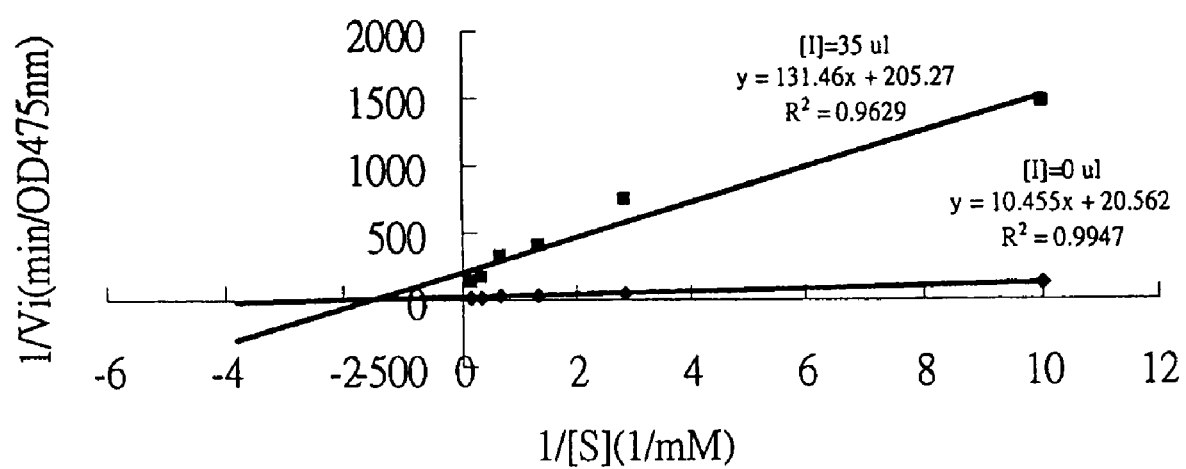
FIG. 3 shows the Lineweaver-Burk plot of the inhibitory effect of the tyrosinase inhibitor extract of the invention on tyrosinase.

Inhibition Pattern of the Tyrosinase Inhibitor Extract 15.1 of 1000 units/ml tyrosinase solution was added to 35 μl of the tyrosinase inhibitor extract of Example 1 and 35 μl of 80% propylene glycol. The resultant solution was reacted at 25. for 1 hour. 450 μl of 16.7 mM potassium phosphate buffer (pH 6.5) (containing 0.1, 0.35, 0.75, 1.5, 3 and 6 mM of L-DOPA and 0.5% Triton X-100) was added to the resulting solution. The related data are shown in the table below:

In addition, FIG. 3 shows the lineweaver-Burk plot. According to the plot, the tyrosinase inhibitor extract of the invention is a non-competitive inhibitor, which can inhibit effectively the synthesis of melanin at a low concentration.

Example 5

Inhibition of the Tyrosinase Inhibitor Extract in O-Quinone Pathway

Figure 4:
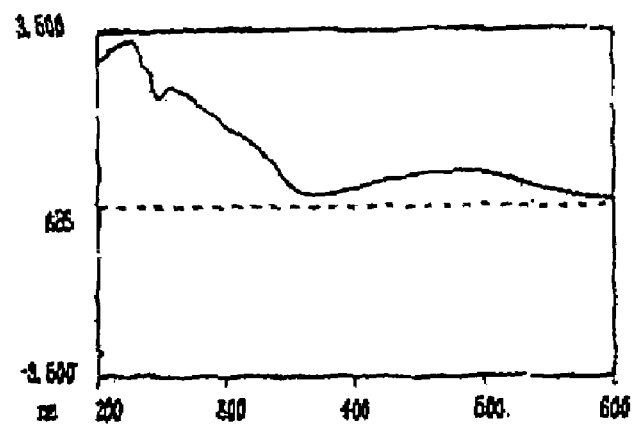
FIGS. 4A, B, and C, shows the inhibitory effect of the extract of the invention on the synthesis of O-quinone.
Figure 4:
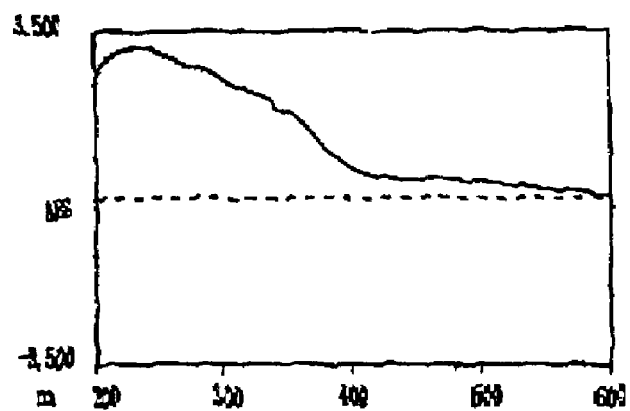
Figure 4:
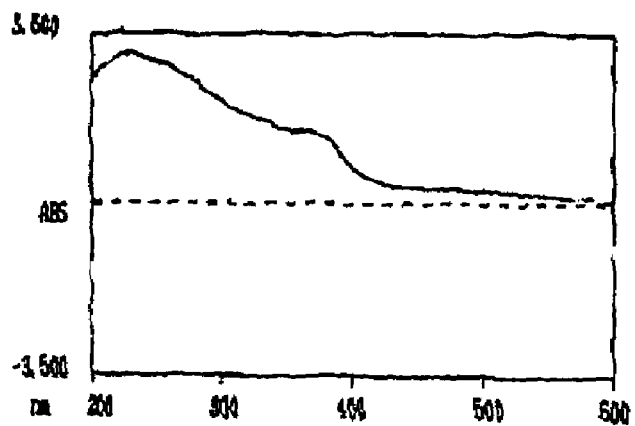

15 μl of tyrosinase solution was added to each of 50 μl and 100 μl of the tyrosinase inhibitor extract of Example 1. The resultant solutions were reacted at 25. for 30 minutes. After reaction, 450 μl of 16.7 mM potassium phosphate buffer (pH 6.5) containing 3.4 mM L-DOPA and 0.5% Tration X-100 was added to the solutions. The absorbance at wavelengths 200 nm to 600 nm of the extracts is shown in FIGS. 4A, 4B and 4C. The absorbance peak for O-quinone is at the wavelength 475 nm.

As shown in FIGS. 4A, 4B, and 4C, the absorbance is dose dependent and reversely proportional to its concentration. As the concentration of the tyrosinase inhibitor extract invention increases, the absorbance decreases. Therefore, the tyrosinase inhibitor extract of the invention inhibits the synthetic pathway of O-quinone catalyzed by tyrosinase.

Example 6

Comparison on Inhibitory Activity between the Tyrosine Extract and Arbutin

The inhibitory percentage of the tyrosinase inhibitor extract and arbutin was determined in a way described in Example 4. The inhibitory percentage of the tyrosinase inhibitor extract and arbutin are shown in the table below:
Sample % inhibitory Activity
Tyrosinase Inhibitor Extract 90.3+−0.3
Arbutin 32+−0.0

What is claimed is:

1. A tyrosinase inhibitor extract, which is obtainable by the process comprising the steps of:
    a) mixing lemon peels with a propylene glycol solution;
    b) breaking the cell walls of the lemon peels whereby the tyrosinase inhibitor content therein is extracted into the propylene glycol solution; and
    c) removing the lemon peels.

2. The tyrosine inhibitor extract of claim 1, wherein the lemon peels are optionally cut into pieces.

3. The tyrosine inhibitor extract of claim 1, wherein the concentration of propylene glycol in the solution is higher than 50%.

| Substrate Conc. [S] (mM) | Initial Velocity Control Sample O.D.475/min | Initial Velocity Tyrosinase Inhibitor Extract O.D.475/min | I/Vi Control O.D.475/min | I/Vi Tyrosinase Inhibitor Extract O.D.475/min |
|---|---|---|---|---|
| 0.10 | 0.008 | 0.0007 | 124.40 | 1471.35 |
| 0.35 | 0.018 | 0.0013 | 54.17 | 746.55 |
| 0.75 | 0.033 | 0.0025 | 30.68 | 403.71 |
| 1.50 | 0.033 | 0.0030 | 30.62 | 329.92 |
| 3.00 | 0.043 | 0.0061 | 23.13 | 165.08 |
| 6.00 | 0.048 | 0.0075 | 20.92 | 133.87 |

4. The tyrosine inhibitor extract of claim 1, wherein the concentration of propylene glycol in the solution is higher than 70%.

5. The tyrosine inhibitor extract of claim 1, wherein the concentration of propylene glycol in the solution is higher than 80%.

6. The tyrosine inhibitor extract of claim 1, wherein the ratio of the lemon peels to the propylene glycol solution ranges from 0.1 g/ml to 1 g/ml.

7. The tyrosine inhibitor extract of claim 1, wherein the ratio of the lemon peels to the propylene glycol solution ranges from 0.2 g/ml to 0.8 g/ml.

8. The tyrosine inhibitor extract of claim 1, wherein the cell walls of lemon peels are broken by sonication, Waring blender, homogenization, French press or Polytron.

9. The tyrosine inhibitor extract of claim 1, wherein the cell walls of lemon peels are broken by sonication and homogenization.

10. The tyrosine inhibitor extract of claim 1, wherein the resultant solution of step b) is further sterilized.

11. The tyrosine inhibitor extract of claim 10, wherein the sterilization is performed by microwave, filtration, UV or gamma radiation.

12. The tyrosine inhibitor extract of claim 10, wherein the sterilization is performed by microwave.

13. The tyrosine inhibitor extract of claim 1, wherein the lemon peels are removed by centrifugation or filtration.

14. The tyrosine inhibitor extract of claim 1, wherein the lemon peels are removed by centrifugation.

15. A process for preparing a tyrosinase inhibitor extract, comprising the steps of:
   a) mixing lemon peels with a propylene glycol solution;
   b) breaking the cell walls of the lemon peels whereby the tyrosinase inhibitor content therein is extracted into the propylene glycol solution; and
   c) removing the lemon peels.

16. The process of claim 15, which further comprises before step c), a step of sterilizing the resultant solution of step b).

* * * * *